US011002742B2

(12) United States Patent
Kimzey et al.

(10) Patent No.: US 11,002,742 B2
(45) Date of Patent: May 11, 2021

(54) COMPOUND FOR LABELING AMINE-CONTAINING COMPOUNDS, AND ITS USE

(71) Applicant: ProZyme, Inc., Hayward, CA (US)

(72) Inventors: Michael J. Kimzey, Oakland, CA (US); Alexander Gyenes, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 472 days.

(21) Appl. No.: 15/575,355

(22) PCT Filed: May 27, 2016

(86) PCT No.: PCT/US2016/034706
§ 371 (c)(1),
(2) Date: Nov. 18, 2017

(87) PCT Pub. No.: WO2016/196311
PCT Pub. Date: Dec. 8, 2016

(65) Prior Publication Data
US 2018/0156809 A1 Jun. 7, 2018

Related U.S. Application Data

(60) Provisional application No. 62/168,654, filed on May 29, 2015.

(51) Int. Cl.
*G01N 33/58* (2006.01)
*C07D 207/46* (2006.01)

(52) U.S. Cl.
CPC ......... *G01N 33/582* (2013.01); *C07D 207/46* (2013.01); *G01N 2400/10* (2013.01); *G01N 2458/00* (2013.01)

(58) Field of Classification Search
CPC ............. G01N 33/582; G01N 2458/00; G01N 2400/10; C07D 207/46
See application file for complete search history.

(56) References Cited

U.S. PATENT DOCUMENTS

| | | |
|---|---|---|
| 5,283,068 A | 2/1994 | Koch |
| 5,296,599 A | 3/1994 | Cohen |
| 6,048,707 A | 4/2000 | Klock, Jr. |
| 8,124,792 B2 | 2/2012 | Baginski |
| 8,445,292 B2 | 5/2013 | Baginski |
| 9,658,234 B2 | 5/2017 | Miyano |
| 2014/0038215 A1 | 2/2014 | Smart |
| 2014/0179011 A1 | 6/2014 | Brousmiche |
| 2014/0242709 A1 | 8/2014 | Brousmiche |
| 2014/0350263 A1 | 11/2014 | Brousmiche |
| 2016/0139136 A1 | 5/2016 | Brousmiche |

FOREIGN PATENT DOCUMENTS

| | | |
|---|---|---|
| EP | 2252584 B1 | 12/2016 |
| EP | 2761296 B1 | 8/2017 |
| JP | H10-306075 | 11/1998 |
| WO | 2013049622 A1 | 4/2013 |

OTHER PUBLICATIONS

Klapoetke et al., "The evaluation of a novel approach for the profiling and identification of N-linked glycan with a procainamide . . . ," J Pharm Biomed Anal, 2010, 53:315-324.
Pabst, et al., "Comparison of fluorescent labels for oligosaccharides and introduction of a new postlabeling purification method," Analytical Biochemistry, 2009, 384:263-273.
Keough et al., "Atmospheric Pressure Matrix-Assisted Laser Desorption/Ionization Ion Trap Mass Spectrometry of Sulfonic Acid . . . ," Rapid Comm Mass Spec, 2001, 15:2227-2239.
Yost and Enke, "Triple Quadrupole Mass Spectrometry for Direct Mixture Analysis and Structure Elucidation," Analytical Chemistry, 1979, 51(12):1251A-1264A.
Baxter, Excerpt of prosecution file history of U.S. Appl. No. 15/003,235, now U.S. Pat. No. 9,658,234.
Shier/Wallenhorst, Excerpt of prosecution file history of U.S. Appl. No. 10/918,380, now U.S. Pat. No. 7,148,069.
Baxter, Excerpt of prosecution file history of U.S. Appl. No. 11/514,130, now U.S. Pat. No. 9,274,123.
Ma and Lau, "Determination of Midazolam and its Metabolites in Serum Microsamples by High-Performance Liquid . . . ," J Chromatography B Biomed Appl, 1996, 682(1):109-113.
Buku et al., 2,3-trans-3,4-trans3,4-Dihydroxy-L-proline: An Amino Acid in Toxic Peptides of Amanita virosa Mushrooms, Proc Natl Acad Sci USA, 1980, 77(5):2370-2371.
Yates et al., "Peptide Mass Maps: A Highly Informative Approach to Protein Identification," Analytical Biochemistry, 1993, 214:397-408.
Cech and Enke, "Relating Electrospray Ionization Response to Nonpolar Character of Small Peptides," Anal. Chem., 2000, 72:2717-2723.
Non-final office action dated Nov. 4, 2016, U.S. Appl. No. 14/342,131.
"Response to Office Action dated Nov. 4, 2016," dated Feb. 6, 2017, U.S. Appl. No. 14/342,131.
USPTO, Final office action dated Apr. 4, 2017, U.S. Appl. No. 14/342,131.
Carol M. Nielsen, "Response to Office Action dated Apr. 4, 2017, Made Final," dated Jun. 5, 2017, U.S. Appl. No. 14/342,131.
Advisory Action, dated Jun. 26, 2017, U.S. Appl. No. 14/342,131.
Carol M. Nielsen, RCE and "Response to Office Action dated Apr. 4, 2017, Made Final," dated Jul. 5, 2017, U.S. Appl. No. 14/342,131.
Non-Final Office Action, dated Aug. 30, 2017, U.S. Appl. No. 14/342,131.

(Continued)

*Primary Examiner* — Christopher Adam Hixson
*Assistant Examiner* — Michelle Adams
(74) *Attorney, Agent, or Firm* — Laurence J. Hyman; Hyman IP Law (57) ABSTRACT

The invention relates to an activated form of procaine, and the use of the activated procaine, or salts or solvates thereof, to label amine-containing compounds, such as N-glycans, amine-containing amino acids, amine-containing peptides, amine-containing proteins, or other amine-containing compounds in a sample. Use of activated procaine as a label allows for sensitive detection of compounds labeled with it both by fluorescence and by mass spectrometry.

24 Claims, 2 Drawing Sheets

(56) References Cited

OTHER PUBLICATIONS

Nimura et al., "Activated Carbamate Reagent as Derivatizing Agent for Amino Compounds in High-Performance Liquid Chromatography," Anal. Chem. 1986, 58:2372-2375.
Liu et al., "Femtomole Peptide Mapping by Derivatization, High-Performance Liquid Chromatography, and Fluorescence Detection," Anal. Biochem. 2001, 294:7-18.
Roth et al., "Charge Derivatization of Peptides for Analysis by Mass Spectrometry," Mass Spectrometry Reviews, 1998, 17:255-274.
Schwartz et al., "Systemic Delineation of Scan Modes in Multidimensional Mass Spectrometry," Anal. Chem., 1990, 62:1809-1818.
Cohen et al., "Clearing the Hurdle of High Sensitivity in Biopharmaceutical Research," LC GC North America, 1999, 17(4S):S9-S16.
Lawrence "Derivitization in Chromatography Introduction, Practical Aspects of Chemical Derivatization in Chromatography," J Chromatogaphic Sci, 1979, 17:113-114.
Jupille, "UV-Visible Absorption Derivitization in Liquid Chromatography," J Chromatogaphic Sci, 1979, 17:160-167.
Fekkes, "State-Of-The-Art of High-Performance Liquid Chromatographic Analysis of Amino Acids in Physiological Samples," J Chromatography B, 1996, 682(1):3-22.
Covey et al., Liquid Chromatography/Mass Spectrometry, Analytical Chemistry, 1986, 58(14):1451A-1461A.
Chalmers and Gaskell, "Advances in Mass Spectrometry for Proteome Analysis," Curr Opinion in Biotech, 2000, 11:384-390.

COMPOUND FOR LABELING AMINE-CONTAINING COMPOUNDS, AND ITS USE

CROSS-REFERENCE TO RELATED APPLICATIONS

This application claims the benefit of U.S. Provisional Application No. 62/168,654, filed May 29, 2015, the contents of which are incorporated herein by reference in their entirety.

STATEMENT OF FEDERAL FUNDING

Not applicable.

BACKGROUND OF THE INVENTION

This invention relates to the field of analysis of glycosylation of amine-containing compounds, such as glycoproteins.

Many of the proteins produced by eukaryotic cells are modified after translation by the addition of covalently-linked, linear or branched chains of carbohydrates. These protein-carbohydrate conjugates are referred to as glycoproteins; the point at which the carbohydrate is attached is referred to as a glycosylation site. Attached polysaccharides or oligosaccharides are referred to as glycans. A wide range of glycans are found on the different glycosylation sites of particular glycoproteins. The particular pattern of glycans on a particular glycoprotein is determined by the specific cell line that produced the protein and the conditions under which the cells were grown.

Since the glycans conjugated to a protein can affect characteristics critical to its function, including pharmacokinetics, stability, bioactivity, or immunogenicity, it is important in many uses to determine which glycans are present. Thus, once glycans have been released from a glycoprotein, it is useful to label them. N-glycans are typically labeled at their free-reducing terminus for analysis by methods such as high performance liquid chromatography (HPLC), capillary electrophoresis (CE), carbohydrate gel electrophoresis, fluorescence analysis, mass spectrometry (MS) and others. The following patent documents describe the labeling of N-glycans: U.S. Pat. Nos. 8,124,792 and 8,445,292, and U.S. Patent Application Publication Nos. 2014/0179011, 2014/0242709, and 2014/0350263; each of these references is incorporated by reference in its entirety.

There is a need in the art for further labels and methods that provide rapid labeling of N-glycans and other amine-containing compounds under mild conditions, without causing the degradation of labile components, and that can provide high sensitivity of detection by both fluorescence and by MS. Surprisingly, the present invention meets these and other needs.

BRIEF SUMMARY OF THE INVENTION

This invention describes novel compounds for labeling N-glycans, amine-containing amino acids, peptides, proteins, and other amine containing compounds, that allow the rapid detection, identification and quantification of the amine containing compounds by analytical means, and particularly by both fluorescence and mass spectrometry. The compounds provide a superior combination of sensitivity of detection by different analytical techniques over other labels now currently used in the art.

In some embodiments, the invention provides a compound, "Activated Procaine," with the structure

(Structure 1)

or a solvate or a salt thereof. In some embodiments, the compound is Activated Procaine. In some embodiments, the compound is a solvate of Activated Procaine. In some embodiments, the compound is a salt of Activated Procaine.

In some embodiments, the invention provides methods for labeling and, optionally, analyzing, an N-glycan, an amine-containing amino acid, peptide, protein, or other amine-containing compound, in a sample comprising: reacting said N-glycan, amine-containing amino acid, peptide, protein, or other amine-containing compound with a compound ("Activated Procaine")

(Structure 1)

or a solvate or a salt thereof, thereby labeling said N-glycan, amine-containing amino acid, peptide, protein, or other amine-containing compound in the sample. In some embodiments, the compound is Activated Procaine. In some embodiments, the compound is a solvate of Activated Procaine. In some embodiments, the compound is a salt of Activated Procaine. In some embodiments. N-hydroxysuccinimide is present when the Activated Procaine or solvent or salt thereof is reacted with the amine-containing compound. In some embodiments, the Activated Procaine or a solvate or salt thereof labels the N-glycan. In some embodiments, the Activated Procaine or a solvate or salt thereof labels a peptide or protein at its N-terminus. In some embodiments, the methods further comprise analyzing the labeled N-glycan, amine-containing amino acid, peptide, protein, or other amine-containing compound by providing the N-glycan, amine-containing amino acid, amine-containing peptide, amine-containing protein, or other amine-containing compound to an analytical means. In some embodiments, the analytical means is selected from the group consisting of high-pressure liquid chromatography, capillary electrophoresis, fluorescence analysis, mass spectrometry, and a combination of any of these. In some embodiments, the combination is of fluorescence analysis and mass spectrometry.

In some embodiments, the invention provides methods for analyzing one or more N-glycans, amine-containing amino acids, peptides, proteins, or other amine-containing compounds in a sample, comprising: (i) contacting said N-glycan, amine-containing amino acids, peptides, proteins, or other amine-containing compounds in said sample with a compound ("Activated Procaine")

(Structure 1)

or a solvate or a salt thereof, under conditions sufficient to label the N-glycans, amine-containing amino acids, peptides, proteins, or other amine-containing compounds in the sample, (ii) subjecting the aid labeled N-glycans, amine-containing amino acids, peptides, proteins, or other amine-containing compounds to chromatographic means, thereby separating them, and (iii) measuring the fluorescence intensity of one or more of the separated labeled N-glycans, amine-containing amino acids, peptides, proteins, or other amine-containing compounds in the sample, thereby analyzing one or more of the N-glycans, amine-containing amino acids, peptides, proteins, or other amine-containing compounds in the sample. In some embodiments, the compound is Activated Procaine. In some embodiments, the compound is a solvate of Activated Procaine. In some embodiments, the compound is a salt of Activated Procaine. In some embodiments, N-hydroxysuccinimide is present when the N-glycans, amine-containing amino acids, peptides, proteins, or other amine-containing compounds are contacted with the Activated Procaine or solvate or salt thereof. In some embodiments, the methods further comprise step (iv), subjecting the one or more labeled N-glycans, amine-containing amino acids, peptides, proteins, or other amine-containing compounds to mass spectrometry to identify the one or more said labeled N-glycans, amine-containing amino acids, peptides, proteins, or other amine-containing compounds. In some embodiments, one or more peptides or proteins are labeled at the N-terminus. In some embodiments, the methods further comprise step (v), subjecting one or more of said separated released labeled N-glycans to mass spectrometry to identify the labeled N-glycans. In some embodiments, the methods further comprise releasing of the N-glycans from said glycoprotein by digestion with a deglycosylation enzyme. In some embodiments, the deglycosylation enzyme is PNGase F. In some embodiments, the glycoprotein is immobilized on a solid support. In some of these embodiments, the released N-glycans are eluted from the immobilized glycoprotein.

In some embodiments, the invention provides kits for labeling a compound of interest selected from the group consisting of an N-glycan, an amine-containing amino acid, a peptide, a protein, and another amine-containing compound in a sample. The kits comprise:

(i) a labeling compound with the structure (Structure 1)

("Activated Procaine") or a solvate or a salt thereof, and (ii) instructions for labeling the N-glycan, amine-containing amino acid, peptide, protein, or other amine-containing compound with said labeling compound. In some embodiments, the kit further comprises N-hydroxysuccinimide. In some embodiments, the instructions are for labeling an N-glycan. In some embodiments, the kit further comprises PNGase F.

BRIEF DESCRIPTION OF THE DRAWINGS

FIG. 1 presents the fluorescent peak area of G0F released from etanercept and then labeled with one of four labels: Activated Procaine, RAPIFLUOR-MS®, procainamide, and 2-AB, as shown in the labels of the bars of the graph, reading from left to right. The scale on the Y axis is linear. The error bars show one standard deviation of the results using four replicates for each label.

DETAILED DESCRIPTION

A. Introduction

The present disclosure relates to compounds that are surprisingly superior for their ability to label N-glycans, amine-containing amino acids, amine-containing peptides, amine-containing proteins, and other amine containing compounds, with the resulting labeled compound being easier to detect by fluorescence, by mass spectrometry ("MS"), or by other analytical means than are amine-containing compounds labeled by other labels currently used in the art for these purposes, and to methods using these compounds. The inventive compounds provide the unique ability to detect amine-containing compounds labeled with the inventive compounds over previously available labels by a multiplicity of analytic techniques. In particular, the inventive compounds provide surprisingly better detection by fluorescence of amine-containing compounds labeled with the inventive compounds compared to other labels currently used to label amine-reactive compounds, while providing detection by MS at least equivalent to that of currently available labels, including a reagent specifically promoted for the sensitivity of its detection by MS and the combination of that capability with detection by fluorescence. Accordingly, the inventive compounds provide a unique and surprisingly superior solution to the problem of labeling amine-containing compounds, and particularly N-glycans, with a single label that allows sensitive detection of the amine-containing compound by two of the analytic methods most commonly used in the art to quantitate and identify amine-containing compounds in general and N-glycans in particular.

The inventive compounds are related to the following structure:

Hereinafter, this compound will be referred to as Activated Procaine. In some embodiments, the label used to label an amine-containing compound of interest, such as an N-glycan, is Activated Procaine.

In some embodiments, a solvate of Activated Procaine is used to label an amine-containing compound of interest. In addition to unsolvated forms, Activated Procaine can exist in solvated forms with pharmaceutically acceptable solvents such as water, ethanol, and the like. In general, the solvated forms are considered equivalent to the unsolvated forms for the purposes of labeling N-glycans.

In some embodiments, a salt of Activated Procaine, in particular an acid addition salt, is used to label an amine-containing compound of interest, and in particular, an N-glycan of interest. Examples of acids which can be employed to form a salt of Activated Procaine include inorganic acids and organic acids known to those skilled in the art such as, but not limited to, hydrochloric, hydrofluoric, hydroiodic, hydrobromic, sulfuric, hydrosulfuric, thiosulfuric, hydrocyanic, phosphoric, phosphorous, hydrochlorous, chlorous, nitrous, nitric, chloric, perchloric, sulfurous, oxalic, maleic, succinic, and citric.

In addition, other acids can form a salt including, but not limited to, 1-hydroxy 2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, isobutyric acid, lactic acid (DL), lactobionic acid, lauric acid, maleic acid, malic acid (−L), malonic acid, mandelic acid (DL), methane sulfonic acid, naphthalene-1,5, disulfonic acid, naphthalene 2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), undecylenic acid.

In some embodiments, N-hydroxysuccinimide is present when the Activated Procaine or solvent or salt thereof labels the N-glycans, amine-containing amino acids, amine-containing peptides, amine-containing proteins, or other amine containing compound. Activated Procaine and salts and solvates thereof are referred to collectively herein as the "Compounds."

The ability of any particular solvate or salt of Activated Procaine to act as a label can be readily tested by, for example, by preparing replicate samples of a selected N-glycan, dividing the replicate samples into two groups, labeling the replicates in the first group with the Activated Procaine solvate or salt and labeling the replicates in the second group with Activate Procaine, measuring the fluorescent intensity of each replicate in each group, and comparing the fluorescent intensity of the replicates in each group, with labels having higher intensity compared to Activated Procaine being considered a better label and more preferred, while labels with lower intensity compared to Activated Procaine being considered not as good a label and less preferred.

B. Synthesis

Activated Procaine can be synthesized by well-known methods. The compound procaine (2-(diethylamino)ethyl 4-aminobenzoate, CAS No. 59-46-1) is commercially available from various manufacturers and distributors, including Sigma-Aldrich Corp. (St. Louis, Mo.) and Key Organics Ltd. (Camelford, Cornwall, United Kingdom). Activated procaine is synthesized by reacting procaine with N,N'-disuccinimidyl carbonate (also available from, e.g., Sigma-Aldrich), by means known in the art. For example, similar reactions are carried out in Schemes 1 and 2 of U.S. Pat. No. 8,124,792 and in Scheme II in US Patent Publication No. 20140350263, each of which is hereby incorporated by reference. The solvates and salts of Activated Procaine can be made by methods well known in the art, such as by mixing Activated Procaine with the solvent or with the acid. N-hydroxysuccinimide occurs as a byproduct of the synthesis. In some embodiments, it may not be purified out from the solution containing the Activated Procaine or solvate or salt thereof and is present when the Activated Procaine or solvate or salt thereof is used to label an amine-containing compound. If any N-hydroxysuccinimide has been purified out prior to labeling of an amine-compound and its presence during the labeling is desired, it can be added prior to the labeling.

C. Uses and Applications of the Compounds

1. Introduction

The Compounds are fluorescent, MS active compounds useful in rapid tagging of glycans such as N-linked glycans and other bio-molecules, including N-glycans, amine-containing amino acids, amine-containing peptides, amine-containing proteins, and other amine containing compounds. These fluorescent, MS active Compounds have three functional components: (a) a succidimidyl-carbamate group; (b) a highly fluorescent moiety, and (c) and a tertiary amino group moiety which is MS active (referring to the structure of Activated Procaine shown above, these three components of the molecule are seen left-to-right). The succidimidyl-carbamate group provides rapid tagging of amine-containing compounds, the fluorescent moiety provides for a strong fluorescent signal, and the tertiary amino group provides a strong MS signal. These three components of Activated Procaine are helpful in analyzing N-glycans, amine-containing amino acids, amine-containing peptides and proteins, and other amine containing compounds.

Amine-containing compounds labeled using the inventive Compounds can be analyzed by a number of techniques known in the art. With recent advancements in mass spectrometry instrumentation, the combination of liquid chromatography to separate labeled compounds, fluorescence measurement to quantitate the separated compounds, and MS to identify them, has gained popularity as a workflow for characterization of compounds such as N-glycans. Fluorescent measurements are sensitive and quantitative; the low detection limit is in the low femtomoles, while MS measurements facilitate identification of the labeled compound. The inventive Compounds allow relative quantitation and molecular weight measurements to be made using a single label, with superior overall detection compared to other labels.

The Compounds are particularly useful in analyzing N-glycans in research on and production of glycosylated proteins, such as monoclonal antibodies. While the studies reported in the Examples use an N-glycan as an exemplar amine-containing compound, it is expected that the succidimidyl-carbamate group of the inventive Compounds will react with amines on most amine-containing compounds.

In some embodiments, the practitioner may wish to analyze either the N-glycans on a glycoprotein, the protein component of the glycoprotein remaining following release of the N-glycans, or both. In such embodiments, the N-glycans can be released from the glycoprotein by enzymatic digestion, separated from the glycoprotein, and the separated N-glycans, or the separated glycoprotein, or both can then be labeled by the inventive Compounds and methods, as described herein. For example, a glycoprotein can be immobilized on a solid support, such as a bead or a membrane, prior to deglycosylation and subjected to deglycosylation by, for example, contacting the glycoprotein with a deglycosylation enzyme, such as PNGase F. The released glycans can then be eluted away from the immobilized glycoprotein and labeled with one of the inventive Compounds. The glycoprotein can then itself be labeled by one of the inventive Compounds, either after being released from the solid support or while it is still immobilized.

2. Labeling Peptides and Proteins

In some uses, the practitioner may wish to label a peptide or protein for detection by analytical means, such as detection of fluorescence and mass spectrometry. The inventive Compounds and methods can be used to label peptides and proteins for detection by these and other analytical methods.

Peptides and proteins are linear polymers of amino acid residues and have a carboxy end and an amino end with a free amino group. The amino end with the free amino group is referred to as the "amino-terminus" or the "N-terminus". It is expected that the inventive Compounds and methods can be used to label the free amino group on the N-terminus of any peptide or protein in which the N-terminus has not been modified co- or post-translationally with a chemical group or molecule that removes the free amine group of the peptide or protein or that renders it inaccessible. Peptides and proteins containing a free amino group on their N-terminus are thus considered to be "amine-containing compounds" which can be labeled by the inventive Compounds and methods.

Further, many peptides and most proteins also contain one or more lysine, arginine, or histidine residues, each of which has an amine group available for labeling. The protein will typically be labeled by the Compounds at any lysine residues, and typically also at histidine and arginine residues present in the glycoprotein (lysine is the most active residue in reacting with the Compounds and may be labeled even if arginine and histidine residues are not labeled). Thus, it is expected that the Compounds will label peptides or proteins at both the N-terminus and at any lysine residues and often at any histidine and arginine residues as well. Further, it is expected that the inventive Compounds and methods can be used to label the lysine residues, and often the histidine and arginine residues, in peptides and proteins containing such residues, even if the amine group in the N-terminus has been modified such that the N-terminus itself cannot be labeled, and thus are amine-containing compounds which can be labeled by the inventive Compounds and methods. In relatively unusual instances, a peptide or protein may have an N-terminus in which the amine group is chemically modified or blocked such that it cannot be labeled by the inventive Compounds and methods, and either does not contain a lysine, histidine or arginine residue or has a lysine, arginine or histidine residue that has been chemically modified such that it no longer has an amine group available for reaction with the label. Unless such a peptide or protein bears some other amine group, it will not be susceptible to being labeled by the inventive Compounds and methods. Any particular peptide or protein in which such a situation may be present can readily tested for whether it can be labeled by the inventive Compound and methods by a simple assay, such as the one used in the Examples. In some cases, a peptide or protein may have a secondary, tertiary or quaternary structure that blocks access of the label to the N-terminus. In such cases, the peptide or protein is preferably denatured by any of a number of methods known in the art before being labeled. For example, the peptide or protein can be boiled at 100° C., contacted with a denaturant, such as sodium dodecyl sulfate, or a chaotrope, such as urea, or denatured by a combination of these methods.

Persons of skill can readily determine whether any particular peptide or protein of interest can or cannot be labeled by the inventive Compounds and methods by a simple assay, such as the exemplar assay set forth in the Examples.

3. Labeling Other Amine-Containing Compounds

It is also expected that the inventive Compounds and methods can be used to label compounds other than those listed above so long as the compounds contain one or more amine groups (for convenience of reference, such compounds are referred to herein as "other amine-containing compounds"). O-glycans do not normally contain an amine group. O-glycans can, however, be modified to contain an amine group, which can then be labeled using the inventive Compounds and methods, and the amine-containing form that started as an O-glycan can then be analyzed. As used herein, the phrase "other amine-containing compounds" includes O-glycans that have been modified to contain an amine group. Persons of skill can readily determine whether any particular amine-containing compound cannot be labeled by the inventive Compounds and methods by a simple assay, such as the exemplar assay set forth in the Examples.

D. Methods for Rapid Labeling

The Compounds are particularly useful for labeling glycans, amine-containing amino acids, peptides, proteins, and other amine-containing compounds because they react quickly with the molecules and form stable, highly fluorescent, MS-active, derivatives. The inventive Compounds and methods allow for labeling of N-glycans and other compounds in minutes, compared to traditional protocols, such as reductive amination, which typically call for incubating the N-glycan or other compound with the label for hours. Further, the inventive Compounds and labels can be readily incorporated into workflows, such as those taught in U.S.

Pat. Nos. 8,445,292 and 8,124,792, with respect to other compounds for rapid labeling of N-glycans and other amine-containing compounds.

The general method for an analysis of N-glycans on a glycoprotein using the Compounds consists of several steps: (1) deglycosylating the glycoprotein to be analyzed to release N-glycans from the glycoprotein, (2) forming labeled N-glycans by reacting with the Compounds, (3) separating the different labeled N-glycans from each other by chromatography, such as high performance liquid chromatography, or "HPLC," and (4) quantifying the amount of each separated, labeled glycan using the fluorescent signal from the label. Optionally, the analysis further comprises step (5), subjecting the separated, labeled N-glycans to mass spectrometry to identify the N-glycan. In some embodiments, the protein is immobilized on a solid support, such as a resin that binds proteins, prior to deglycosylation, facilitating separation of the released N-glycans from the glycoprotein. As noted above, the portion of the glycoprotein remaining following release of the N-glycans can also be labeled by reacting it by the Compounds at the N-terminus of the glycoprotein, as well as at any lysine residues, and in some embodiments, also at any histidine and arginine residues present in the glycoprotein and can be analyzed by steps (3), (4) and (5) above.

Without wishing to be bound by theory, it is believed that the amine-containing compound is labeled with the inventive Compound through a reaction in which the amine-containing compound acts as a nucleophile which attacks the activated electrophilic ester carbon (the one adjacent to the succidimidyl group) of the Activated Procaine. It is further believed that this attack results in the release of the NHS leaving group from the Activated Procaine, and the covalent attachment of the fluorescent and tertiary amine moieties of the Activated Procaine to the amine-containing compound. As used herein. "reacting" an amine-containing compound with one of the inventive Compounds means contacting the amine-containing compound with the inventive Compound under conditions sufficient for the amine-containing compound to be labeled with the fluorescent and tertiary amine moieties of the inventive Compound, typically by covalent attachment.

E. Deglycosylating Glycoproteins

Step (1) of the general method set forth in the preceding paragraph refers to deglycosylating glycoproteins to release N-glycans. N-glycans can be released from a glycoprotein of interest by enzymatic or by chemical means. Both such means of releasing N-glycans from glycoproteins are well known in the art. Protocols and workflows for releasing N-glycans from glycoproteins using deglycosylation enzymes have been known in the art for years and it is assumed persons of skill are familiar with the ranges of times, temperatures and pH used in those workflows and protocols. An exemplar protocol is set forth in the Examples.

Enzymatic digestion by enzymatic cleavage is typically achieved with an exoglycosidase, an endoglycosidase, or PNGase F, discussed below. Exemplar endoglycosidases include endo-alpha-N-acetyl-galactosaminidase, Endoglycosidase F1, Endoglycosidase F2, Endoglycosidase F3, and Endoglycosidase H. In some embodiments, the enzyme is the common deglycosylation enzyme PNGase F (Peptide-N4-(acetyl-ß-glucosaminyl)-asparagine amidase, EC 3.5.1.52), which releases N-glycans from the glycoprotein in the form of glycosylamines, which can then be labeled with the inventive Compounds using the inventive methods. Glycosylamines hydrolyze over time. Accordingly, N-glycans released from a glycoprotein as glycosylamines preferably are labeled within 30 minutes of being released from the glycoprotein, with shorter periods, such as about 25 minutes, about 20 minutes, about 15 minutes, or about 10 minutes, being more preferred, in that order, with "about" meaning±2 minutes. In preferred embodiments, the N-glycans are labeled within about 9, 8, 7, 6, 5, 4, 3, 2 or 1 minutes after being released from the glycoprotein, with "about" meaning±30 seconds. In some preferred embodiments, the N-glycans are labeled within 30 seconds after release from the glycoprotein.

In some embodiments in which a glycoprotein has been immobilized on a solid support, the N-glycans which have been released enzymatically can be eluted and separately labeled by the inventive Compounds and methods. In some other embodiments, following enzymatic release, the N-glycans are labeled in the presence of the glycoprotein, after which the N-glycans are eluted for analysis. The labeled glycoprotein can then be released from the support and eluted for provision to an analytical means.

Enzymatic release of glycans is typically used for N-glycans, as there is no enzyme that efficiently releases all O-glycans from a glycoprotein. O-glycans are typically removed by any of a variety of chemical processes, such as hydrozinolysis, and reductive or non-reductive β-elimination, followed by solid phase extraction of the O-glycans. Methods for releasing O-glycans are discussed in, for example, International Publication No. WO 2011/038874 A1.

F. Conditions for Labeling

The inventive Compounds and methods allow the rapid labeling of N-glycans, amine-containing amino acids, peptides, proteins, and amine-containing compounds under mild conditions. Persons of skill are familiar with methods for rapid labeling of N-glycans under mild conditions using other compounds. U.S. Pat. No. 8,124,792 (the "'792 patent"), for example, discusses rapid labeling of N-glycans under mild conditions at col. 22, line 24, to col. 23, line 3, and col. 30, Example 10, to col. 32, Example 13, as do the corresponding portions of U.S. Pat. No. 8,445,292 (each of these patents is incorporated herein by reference). Methods for providing labeled N-glycans to an analytical means are also well-known in the art, as exemplified by the teachings of the '792 patent at col. 23, line 41 to line 67 and col. 32. Examples 13 and 14.

The Compounds can generally be used as labels using the conditions set forth in the patents discussed above. The labeling can be conducted at about 10°-60° C., preferably at 45° to 55° C., more preferably at about 50° C., with "about" meaning±2° C. and most preferably at 50° C. The labeling is preferably conducted at a pH of 7 to about pH 9, more preferably pH 7.5-8.5, and still more preferably about pH 8, with about meaning±pH 0.25. Most preferably, the pH is 8. The labeling should be allowed to proceed for 30 seconds to 5 minutes, with about 1 to about 3 minutes (with "about" meaning±15 seconds) being more preferred at temperatures of room temperature or above and times on the shorter time of the range stated being preferred when temperatures higher than 40° C., as times on the longer end of the range can lead to "double labeling" or other labeling artifacts.

In the studies reported in the Examples, Activated Procaine was added to glycan samples and labeling was allowed to proceed for 3 minutes at room temperature. In later studies, it was discovered that even better results than those reported in the Examples were obtained when the Activated Procaine was added to the glycan sample and the mixture was then placed on a heat block set at 50° C. for 1 minute. Thus, in preferred embodiments, the solution containing the inventive Compound, such as Activated Procaine, and the N-glycan, peptide, protein or other amine-containing compound to be labeled, is heated to about 50° C. for about 30 seconds to about 3 minutes. In some embodiments, the solution is heated at 50° C. for about 1 minute, with "about" meaning±15 seconds, more preferably ±10 seconds and most preferably ±5 seconds.

Following labeling, water is added to dilute the reactants and bring the volume up to a pre-determined amount before taking samples to be introduced into the analytical instrument or instruments by which the practitioner intends to analyze the labeled compound or compounds. Analyses such as measuring fluorescent intensity and performing mass spectrometry are commonly performed in the art and persons of skill are well familiar with preparing samples of N-glycans and other compounds for such analysis, including bringing the samples up to pre-determined equal volumes before introducing an aliquot volumes into the instrument. In the studies reported in the Examples, after labeling, the volume of each replicate was brought up to 100 µl before an aliquot was taken and introduced into the analytical instrumentation, but the volume will depend on the quantity of the initial reactants and the system on which the labeled compounds are to be analyzed. A dilute acid, such as acetic acid, can be used in place of water to bring the volume up to the pre-determined volume.

G. Kits

Conveniently, one or more of the inventive Compounds can be provided in kits either in dried form or in solution that can be added directly to a sample of the compound which is to be labeled. The kits can further provide instructions for labeling the amine-containing compound of interest with the inventive Compound or Compounds provided. For example, the kits can include directions on using the Compounds to label an N-glycan. The kit may also include reagents, such as PNGase F or one or more other deglycosylation enzymes, to facilitate release and labeling of glycans from a glycoprotein.

EXAMPLES

Example 1

This Example presents the materials and methods used in studies comparing the labeling of N-glycans released from an exemplar FDA-approved therapeutic glycoprotein, etanercept, by four labels: two "rapid labeling" reagents, Activated Procaine and RAPIFLUOR-MS®, (Waters Corp., Milford, Mass.), and two reagents which label by reductive amination, procainamide (4-amino-N-(2-diethylaminoethyl) benzamide, CAS No. 51-06-9) and 2-aminobenzamide ("2-AB," ProZyme, Inc., Hayward, Calif.).

Multiple samples of fifty micrograms of the fusion glycoprotein etanercept were prepared for glycoanalysis using a modified protocol for the GlykoPrep® Rapid N-glycan Preparation kit (ProZyme, Inc.). Briefly, for each sample, the glycoprotein was immobilized onto resin, the sample was washed, and the immobilized glycoprotein was treated with the deglycosylation enzyme PNGase F at pH 8 and heated to 50° C. for 30 minutes to release glycans from the glycoprotein. PNGase F releases N-glycans from the glycoprotein as glycosylamines. The glycosylamines released from each sample were eluted and then labeled as follows.

A first group of four replicate samples was labeled with Activated Procaine as follows. Activated Procaine was prepared in a dimethylformamide ("DMF")-containing solution at 200 mg/ml and 5 µl of the solution was then added to 10 µl of the released N-glycans at room temperature. Labeling was allowed to proceed for three minutes at room temperature.

A second group of four replicate samples was labeled with RAPIFLUOR-MS®, as follows. (The compound called RAPIFLUOR-MS® is shown in U.S. Published Patent Appln. US2014/0179011 A1, on page 14, top left column, in the embodiment where R=N. The compound is described in its product literature as having an NHS carbamate group, a quinolinyl fluorophore, and a tertiary amine charge tag.) RAPIFLUOR-MST was prepared at 68 mg/ml in DMF and 12 µl was added to 10 µl of the released glycans at room temperature. Labeling was allowed to proceed for three minutes at room temperature.

For the third and fourth groups of four replicate samples each, the glycans released from the glycoprotein as glycosylamines were prepared for labeling by reductive amination. The amine group of the glycosylamines was converted to a reducing end by adding 15 µl of dilute acetic acid to 10 µl of the glycans (in the form of glycosylamines) and incubating the samples with the acid at 50° C. for 10 minutes. The released glycans were then dried down to a powder, which was then resolubilized and labeled by adding a solution containing acetic acid, sodium cyanoborohydride and either procainamide (third sample group) or 2-AB (fourth sample group).

After labeling, all samples were adjusted to 100 µl with water without cleanup. One µl per sample was used for LC, fluorescence, and MS analysis (sometimes known in the art as "LC-FLR-MS"). Fluorescence of the four replicates of each of the four labels was measured using the following excitation wavelength (first number) and emission wavelength (second number):

For Activated Procaine: 285 nm/345 nm.
For RAPIFLUOR-MS®: 265 nm/425 nm.
For Procainamide: 308 nm/359 nm.
For 2-AB: 360 nm/428 nm.
MS was run in positive mode.

Example 2

This Example presents the results of studies of the fluorescent analysis of labeling of glycans released from etanercept using the materials and methods described in Example 1.

The methods described in Example 1 resulted in labeling of N-glycans released from etanercept by PNGase F. The various labeled glycans were separated by high pressure liquid chromatography and one glycan was selected as an exemplar by which to compare the relative efficacy of labeling of the labeling by various labels. The glycan chosen to be the exemplar was asialo-, agalacto-, biantennary complex N-glycan, core-substituted with fucose, alternatively referred to as "G0F," "FA2," "F(6)A2," or "NGA2F," which was selected for analysis as it is present on a number of glycoproteins. For convenience of reference, this glycan is referred to herein and on the Figures as "G0F."

Figure 1:
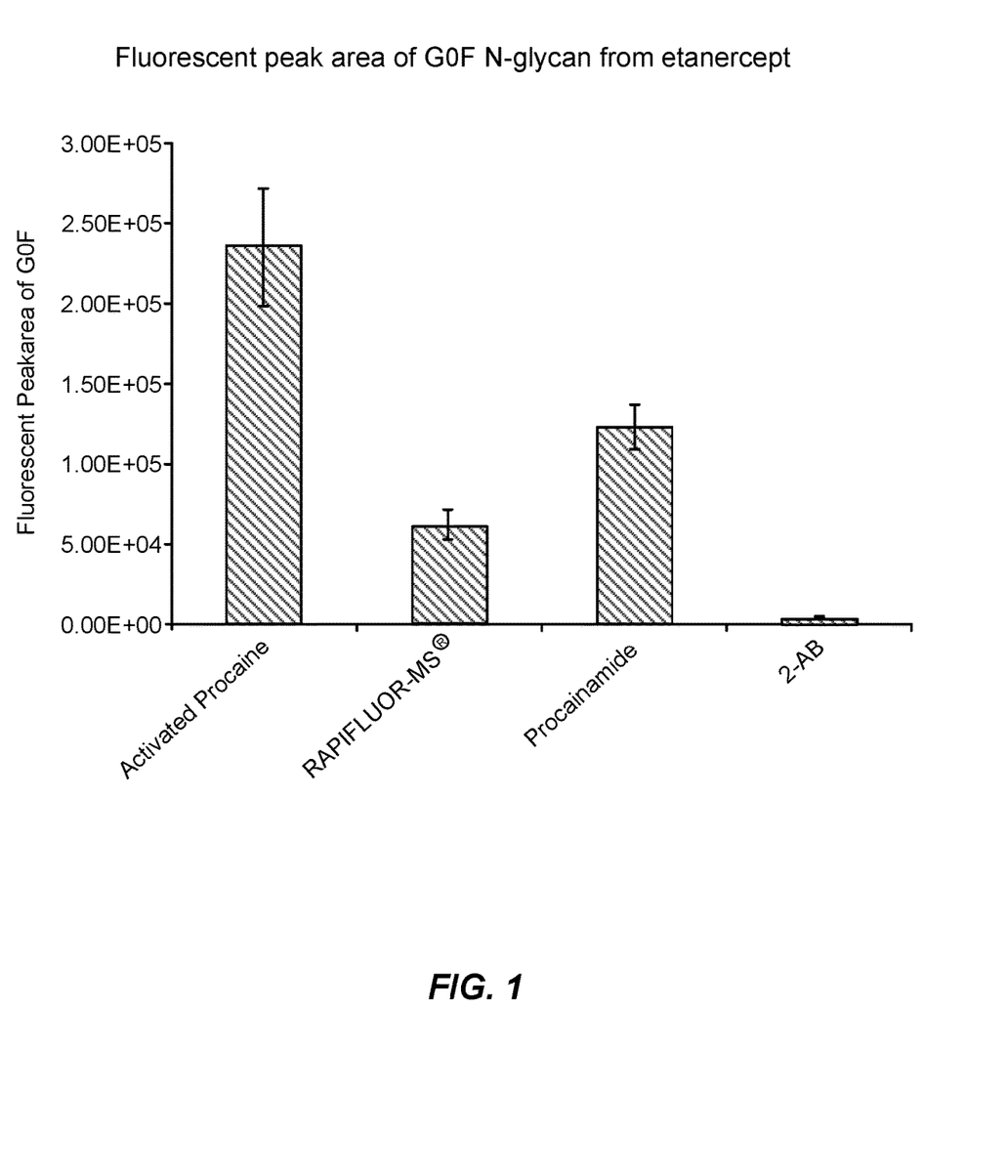
FIG. 1 is a graph presenting the results of studies of the fluorescent labeling of an exemplar N-glycan, asialo-, agalacto-, biantennary complex N-glycan, core-substituted with fucose (for convenience, the N-glycan is abbreviated as "G0F"), released from etanercept by PNGase F.

FIG. 1 presents the fluorescent peak area of G0F N-glycan released from etanercept and labeled with the labels Activated Procaine, RAPIFLUOR-MS®, procainamide, and 2-AB. The scale on the Y axis is linear. The error bars show one standard deviation of the results of the four replicates for each label. As can be seen, the fluorescent peak area of G0F resulting from labeling G0F with Activated Procaine is considerably higher than that resulting from labeling G0F using either RAPIFLUOR-MS® or procainamide and much greater in comparison to the labeling using 2-AB. These results demonstrate that Activated Procaine is significantly better as a label for detecting by fluorescent analysis the presence of a glycan in a sample than are any of the other three labels.

Example 3

This Example presents the results of studies of the mass spectrometry ("MS") analysis of labeling of glycans released from etanercept using the materials and methods described in Example 1.

The methods described in Example 1 resulted in labeling of N-glycans released from etanercept by PNGase F. As in Example 2, to allow comparison of the relative efficacy of labeling, the glycan G0F was selected as the exemplar glycan for analysis, as it is present on a number of glycoproteins.

Figure 2:
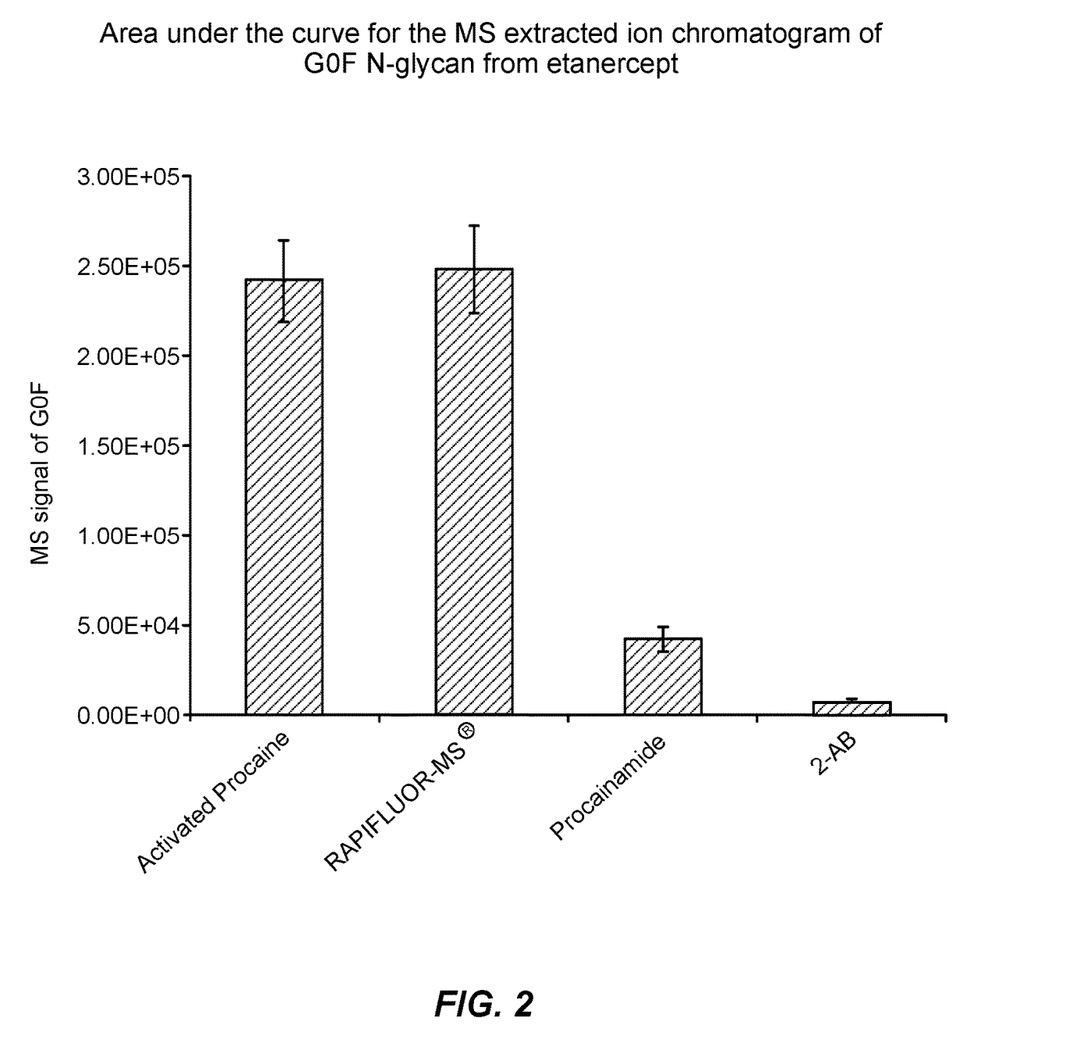
FIG. 2 is a graph presenting the results of studies utilizing mass spectrometry analysis of labeled N-glycans. Specifically, the graph presents the area under the curve for the MS-extracted ion chromatogram of G0F N-glycan released from etanercept and labeled with one of the following labels, reading left to right: Activated Procaine. RAPIFLUOR-MS®, procainamide, and 2-AB. The scale on the Y axis is linear. The error bars show one standard deviation of the results using four replicates for each label.

FIG. 2 is a graph presenting the area under the curve for the MS-extracted ion chromatogram of G0F N-glycan released from etanercept and labeled with the labels Activated Procaine, RAPIFLUOR-MS®, procainamide, and 2-AB. The scale is linear. The error bars show one standard deviation of the results of the four replicates for each label.

As can be seen comparing the first two bars on the left of FIG. 2, the area under the curve for the analysis of G0F resulting from labeling with Activated Procaine is roughly equivalent to the labeling of G0F using RAPIFLUOR-MS®, thus indicating that the two labels are roughly equivalent in labeling the exemplar glycan for detection by MS. Comparing the first bar on the left of FIG. 2 with the third and fourth bars from the left, the area under the curve for the analysis of G0F resulting from labeling with Activated Procaine is significantly greater than the labeling using procainamide or using 2-AB, leading to the conclusion that the labeling of the glycan by Activated Procaine provides significantly superior detection of the presence of the glycan than is afforded either by procainamide or by 2-AB.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A compound ("Activated Procaine") with the structure

(Structure 1)

or a solvate or a salt of said compound.

2. A method for labeling, and optionally, analyzing, an N-glycan, amine-containing amino acid, amine-containing peptide, amine-containing protein, or other amine-containing compound in a sample, said method comprising: reacting said N-glycan, amine-containing amino acid, amine-containing peptide, amine-containing protein, or other amine-containing compound with a labeling compound ("Activated Procaine") with the structure (Structure 1)

or a solvate or a salt of said labeling compound, thereby creating a fluorescent, mass spectrometry-active derivative of said N-glycan, amine-containing amino acid, amine-containing peptide, amine-containing protein, or other amine-containing compound in said sample.

3. The method of claim 2, wherein N-hydroxysuccinimide is present during said reacting of said N-glycan, amine-containing amino acid, amine-containing peptide, amine-containing protein, or other amine-containing compound with said Activated Procaine or solvate or salt thereof.

4. The method of claim 2, wherein said fluorescent, mass spectrometry-active derivative of said N-glycan, amine-containing amino acid, amine-containing peptide, amine-containing protein, or other amine-containing compound is a fluorescent, mass spectrometry-active derivative of said N-glycan.

5. The method of claim 2, wherein said N-glycan, amine-containing amino acid, amine-containing peptide, amine-containing protein, or other amine-containing compound amine-containing compound is an amine-containing peptide or amine-containing protein, which amine-containing peptide or amine-containing protein has an N-terminus and said reacting of said amine-containing peptide or amine-containing protein with said labeling compound occurs at said N-terminus.

6. The method of claim 2, further comprising analyzing said fluorescent, mass spectrometry-active derivative of said N-glycan, amine-containing amino acid, amine-containing peptide, amine-containing protein, or other amine-containing compound by subjecting said fluorescent, mass spectrometry-active derivative of N-glycan, amine-containing amino acid, amine-containing peptide, amine-containing protein, or other amine-containing compound to an analytical method.

7. The method of claim 6, wherein said analytical method is selected from the group consisting of high-pressure liquid chromatography, capillary electrophoresis, fluorescence analysis, mass spectrometry, and a combination of any of these.

8. The method of claim 7, wherein said combination is of fluorescence analysis and mass spectrometry.

9. A method for analyzing N-glycans, amine-containing amino acids, amine-containing peptides, amine-containing proteins, or other amine-containing compounds in a sample, comprising:

(i) contacting said N-glycans, amine-containing amino acids, amine-containing peptides, amine-containing proteins, or other amine-containing compounds in said sample with a labeling compound ("Activated Procaine") with the structure (Structure 1)

or a solvate or a salt of said labeling compound,
under conditions sufficient to create fluorescent, mass spectrometry-active derivatives of said N-glycans, of said amine-containing amino acids, of said amine-containing peptides, of said amine-containing proteins, or of said other amine-containing compounds in said sample, (ii) subjecting said fluorescent, mass spectrometry-active derivatives of said N-glycans, of said amine-containing amino acids, of said amine-containing peptides, of said amine-containing proteins, or of said other amine-containing compounds to chromatographic methods, thereby separating said fluorescent, mass spectrometry-active derivatives of said N-glycans, of said amine-containing amino acids, of said amine-containing peptides, of said amine-containing proteins, or of said other amine-containing compounds, and (iii) measuring fluorescence intensity of said separated fluorescent, mass spectroscopy-active derivatives of said N-glycans, of said amine-containing amino acids, said amine-containing peptides, of said amine-containing proteins, or of said other amine-containing compounds, thereby analyzing said N-glycans, amine-containing amino acids, amine-containing peptides, amine-containing proteins, or other amine-containing compounds in said sample.

10. The method of claim 9, wherein N-hydroxysuccinimide is present during step (i).

11. The method of claim 9, further comprising step (iv):
(iv) subjecting said separated fluorescent, mass spectrometry-active derivatives of said N-glycans, amine-containing amino acids, amine-containing peptides, amine-containing proteins, or other amine-containing compounds to mass spectrometry to identify said separated fluorescent, mass spectrometry-active derivatives of said N-glycans, amine-containing amino acids, amine-containing peptides, amine-containing proteins, or other amine-containing compounds.

12. The method of claim 9, wherein said amine-containing compounds are peptides or proteins each having an N-terminus containing a free amino group, which free amino group is labeled by said labeling compound at said amino group on said N-terminus.

13. A method of analyzing N-glycans present on a glycoprotein, said method comprising:

(i) releasing said N-glycans from said glycoprotein as glycosylamines, thereby obtaining released glycosylamines, (ii) contacting said released glycosylamines with a labeling compound ("Activated Procaine") with the structure (Structure 1)

or a solvate or a salt of said labeling compound,
under conditions sufficient to create fluorescent, mass spectrometry-active derivatives of said released glycosylamines, (iii) subjecting said fluorescent, mass spectrometry-active derivatives of said released glycosylamines to chromatography to obtain separated fluorescent, mass spectrometry-active derivatives of said released glycosylamines, and (iv) measuring a fluorescent signal of said separated fluorescent, mass spectrometry-active derivatives of said released glycosylamines, thereby analyzing said N-glycans present on said glycoprotein.

14. The method of claim 13, wherein N-hydroxysuccinimide is present during step (i).

15. The method of claim 13, further comprising step (v):
(v), subjecting said separated released fluorescent, mass spectrometry-active derivatives of said glycosylamines to mass spectrometry to identify said fluorescent, mass spectrometry-active derivatives.

16. The method of claim 13, wherein said releasing of said N-glycans from said glycoprotein in step (i) is by digestion of said glycoprotein with a deglycosylation enzyme.

17. The method of claim 16, wherein said deglycosylation enzyme is PNGase F.

18. The method of claim 13, wherein said glycoprotein is immobilized on a solid support.

19. The method of claim 18, further comprising eluting said released glycosylamines away from said immobilized glycoprotein prior to step (ii).

20. A kit for labeling a compound of interest selected from the group consisting of an N-glycan, an amine-containing amino acid, an amine-containing peptide, an amine-containing protein, and another amine-containing compound in a sample, said kit comprising:

(i) a container,
(ii) a labeling compound, "Activated Procaine," with the structure (Structure 1)

or a solvate or a salt of said labeling compound, said labeling compound being disposed in said container, and
(iii) instructions for labeling said N-glycan, amine-containing amino acid, amine-containing peptide, amine-containing protein, or other amine-containing compound with said labeling compound.

21. The kit of claim 20, further comprising N-hydroxysuccinimide.

22. The kit of claim 20, wherein said instructions are for labeling an N-glycan released from a glycoprotein or a glycopeptide as a glycosylamine.

23. The kit of claim 20, further comprising an enzyme selected from the group consisting of an endoglycosidase, an exoglycosidase, and PNGase F.

24. The kit of claim 23, wherein said enzyme is PNGase F.

\* \* \* \* \*